United States Patent
Punyani et al.

(10) Patent No.: US 10,258,555 B2
(45) Date of Patent: *Apr. 16, 2019

(54) COMPOSITION FOR HAIR FRIZZ REDUCTION

(71) Applicant: The Procter & Gamble Company, Cincinnati, OH (US)

(72) Inventors: Supriya Punyani, Singapore (SG); Brian Xiaoqing Song, Mason, OH (US); Jennifer Mary Marsh, Deerfield Township, OH (US); Tiffany Tien-Yun Yang, Loveland, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/367,369

(22) Filed: Dec. 2, 2016

(65) Prior Publication Data

US 2017/0157009 A1    Jun. 8, 2017

Related U.S. Application Data

(60) Provisional application No. 62/263,170, filed on Dec. 4, 2015.

(51) Int. Cl.
*A61K 8/365* (2006.01)
*A61K 8/44* (2006.01)
(Continued)

(52) U.S. Cl.
CPC .............. *A61K 8/368* (2013.01); *A61K 8/345* (2013.01); *A61K 8/365* (2013.01); *A61K 8/42* (2013.01);
(Continued)

(58) Field of Classification Search
None
See application file for complete search history.

(56) References Cited

U.S. PATENT DOCUMENTS

| 2,392,314 A | 1/1946 | Dalton |
| 4,496,536 A | 1/1985 | Moller |

(Continued)

FOREIGN PATENT DOCUMENTS

| DE | 19536423 A1 | 4/1996 |
| DE | 102011089357 A1 | 8/2012 |

(Continued)

OTHER PUBLICATIONS ([retrieved from on-line website http://cosmetics.specialchem.com/inci/hydroxyethyl-urea, last visit May 10, 2017]).*

(Continued)

*Primary Examiner* — Ernst V Arnold
*Assistant Examiner* — Kyung S Chang
(74) *Attorney, Agent, or Firm* — Linda M. Sivik

(57) ABSTRACT

The present invention is directed to a shampoo composition for hair frizz reduction comprising from about 0.1% to about 20% of a moisture control material or mixture of moisture control materials wherein the moisture control material is selected from one or more of the following:

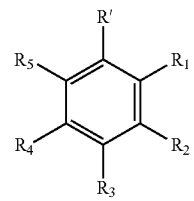

wherein R' is —COOY, sulfonic acid, or C═CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or (Continued)

—CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0.

16 Claims, 1 Drawing Sheet

(51) Int. Cl.
| | | |
|---|---|---|
| A61K 8/46 | (2006.01) | |
| A61Q 5/06 | (2006.01) | |
| A61Q 5/12 | (2006.01) | |
| A61K 8/368 | (2006.01) | |
| A61Q 5/02 | (2006.01) | |
| A61K 8/34 | (2006.01) | |
| A61K 8/89 | (2006.01) | |
| A61K 8/42 | (2006.01) | |
| A61K 8/73 | (2006.01) | |
| A61K 8/81 | (2006.01) | |

(52) U.S. Cl.
CPC .............. *A61K 8/445* (2013.01); *A61K 8/466* (2013.01); *A61K 8/731* (2013.01); *A61K 8/817* (2013.01); *A61K 8/89* (2013.01); *A61Q 5/02* (2013.01); *A61Q 5/06* (2013.01); *A61Q 5/12* (2013.01); *A61K 2800/5426* (2013.01); *A61K 2800/594* (2013.01); *A61K 2800/596* (2013.01)

(56) References Cited

U.S. PATENT DOCUMENTS

| | | | |
|---|---|---|---|
| 4,536,399 A | 8/1985 | Flynn et al. | |
| 4,678,475 A | 7/1987 | Hoshowski et al. | |
| 5,102,655 A | 4/1992 | Yoshihara et al. | |
| 5,384,114 A | 1/1995 | Dowell et al. | |
| 5,587,155 A | 12/1996 | Ochiai et al. | |
| 5,688,495 A | 11/1997 | Rosen et al. | |
| 6,001,340 A | 12/1999 | Rosen et al. | |
| 6,156,299 A | 12/2000 | Rosen et al. | |
| 6,294,186 B1* | 9/2001 | Beerse ................ A01N 43/36 | |
| | | | 424/401 |
| 6,495,498 B2 | 12/2002 | Niemiec et al. | |
| 6,858,202 B2 | 2/2005 | Niemiec et al. | |
| 6,908,889 B2 | 6/2005 | Niemiec et al. | |
| 7,527,654 B2 | 5/2009 | Plos | |
| 8,512,686 B2 | 8/2013 | Morioka | |
| 8,968,712 B2 | 3/2015 | Tanaka | |
| 9,095,528 B2 | 8/2015 | Desenne et al. | |
| 9,216,146 B2 | 12/2015 | Tanaka | |
| 9,259,070 B2 | 2/2016 | Fischer et al. | |
| 9,265,321 B2 | 2/2016 | Fischer et al. | |
| 9,271,908 B2 | 3/2016 | Allef et al. | |
| 9,877,909 B2 | 1/2018 | Cetti et al. | |
| 9,905,528 B2 | 2/2018 | Kira et al. | |
| 10,111,815 B2 | 10/2018 | Marsh et al. | |
| 10,111,820 B2 | 10/2018 | Marsh et al. | |
| 10,117,819 B2 | 11/2018 | Marsh et al. | |
| 2002/0010228 A1 | 1/2002 | Simendinger | |
| 2003/0022936 A1 | 1/2003 | Milbradt et al. | |
| 2003/0143173 A1 | 7/2003 | Buck | |
| 2003/0170195 A1 | 9/2003 | Houze et al. | |
| 2003/0199584 A1 | 10/2003 | Ahluwalia | |
| 2003/0215405 A1 | 11/2003 | Parker et al. | |
| 2003/0223952 A1 | 12/2003 | Wells et al. | |
| 2004/0120911 A1 | 6/2004 | Shah et al. | |
| 2004/0180016 A1 | 9/2004 | Buck | |
| 2004/0261198 A1 | 12/2004 | Kainz et al. | |
| 2005/0136015 A1 | 6/2005 | McKie et al. | |
| 2005/0143268 A1 | 6/2005 | Midha et al. | |
| 2005/0169869 A1 | 8/2005 | Laurent et al. | |
| 2005/0175567 A1* | 8/2005 | Khoshdel ................ A61K 8/347 |
| | | | 424/70.2 |
| 2005/0196369 A1 | 9/2005 | Ueyama et al. | |
| 2005/0266034 A1* | 12/2005 | Muller .................. A61K 8/345 |
| | | | 424/401 |
| 2006/0165636 A1 | 7/2006 | Hasebe et al. | |
| 2006/0204466 A1 | 9/2006 | Littau et al. | |
| 2006/0286059 A1 | 12/2006 | Yang et al. | |
| 2007/0104667 A1 | 5/2007 | Mondet et al. | |
| 2007/0149423 A1 | 6/2007 | Warr et al. | |
| 2007/0261179 A1 | 11/2007 | Dorkel et al. | |
| 2008/0131389 A1 | 6/2008 | Shibuya et al. | |
| 2008/0138438 A1 | 6/2008 | Taylor et al. | |
| 2008/0194454 A1 | 8/2008 | Morgan et al. | |
| 2009/0169502 A1 | 7/2009 | Quadir | |
| 2009/0324531 A1 | 12/2009 | Okada et al. | |
| 2010/0297051 A1 | 11/2010 | Feuillette | |
| 2010/0300472 A1 | 12/2010 | Malle et al. | |
| 2010/0330007 A1 | 12/2010 | Spindler et al. | |
| 2011/0003016 A1 | 1/2011 | Burry et al. | |
| 2011/0226275 A1 | 9/2011 | Fischer et al. | |
| 2011/0256249 A1 | 10/2011 | Campbell et al. | |
| 2011/0269658 A1 | 11/2011 | Dihora et al. | |
| 2011/0274642 A1* | 11/2011 | Yamaki .................... A61K 8/31 |
| | | | 424/70.19 |
| 2012/0070398 A1 | 3/2012 | Nagano et al. | |
| 2012/0093751 A1 | 4/2012 | Nagano et al. | |
| 2012/0308506 A1 | 12/2012 | Oku et al. | |
| 2013/0064908 A1 | 3/2013 | Noh | |
| 2013/0125915 A1 | 5/2013 | Nagase et al. | |
| 2013/0164390 A1 | 6/2013 | Richards et al. | |
| 2013/0167862 A1 | 7/2013 | Lopez et al. | |
| 2013/0259817 A1 | 10/2013 | Uehara et al. | |
| 2013/0259819 A1 | 10/2013 | Uehara et al. | |
| 2013/0306095 A1 | 11/2013 | Syed | |
| 2013/0309190 A1 | 11/2013 | Dimotakis et al. | |
| 2014/0079660 A1 | 3/2014 | Doi | |
| 2014/0154197 A1 | 6/2014 | Swaile et al. | |
| 2014/0179645 A1 | 6/2014 | Arndt | |
| 2014/0335042 A1 | 11/2014 | Peffly | |
| 2015/0174052 A1 | 6/2015 | Mette et al. | |
| 2015/0313832 A1 | 11/2015 | Hilvert et al. | |
| 2015/0359716 A1 | 12/2015 | Marsh et al. | |
| 2015/0374609 A1 | 12/2015 | Cetti et al. | |
| 2016/0015608 A1 | 1/2016 | Marsh et al. | |
| 2016/0022558 A1 | 1/2016 | Kunin et al. | |
| 2016/0158128 A1 | 6/2016 | Marsh et al. | |
| 2016/0158135 A1 | 6/2016 | Marsh et al. | |
| 2016/0175209 A1 | 6/2016 | Walker et al. | |
| 2016/0228342 A1 | 8/2016 | Rose | |
| 2016/0287494 A1 | 10/2016 | Punyani et al. | |
| 2016/0287495 A1 | 10/2016 | Punyani et al. | |
| 2017/0157008 A1 | 6/2017 | Punyani et al. | |
| 2017/0157009 A1 | 6/2017 | Punyani et al. | |
| 2017/0157011 A1 | 6/2017 | Punyani et al. | |
| 2017/0216172 A1 | 8/2017 | Carballada et al. | |
| 2017/0281523 A1 | 10/2017 | Punyani et al. | |
| 2017/0290755 A1 | 10/2017 | Soh et al. | |
| 2018/0289603 A1 | 10/2018 | Punyani et al. | |
| 2018/0289605 A1 | 10/2018 | Punyani et al. | |

FOREIGN PATENT DOCUMENTS

| | | |
|---|---|---|
| EP | 1787680 A2 | 5/2007 |
| EP | 1326577 B1 | 10/2008 |
| EP | 2036536 A1 | 3/2009 |
| EP | 2392314 A1 | 12/2011 |
| FR | 2931659 B1 | 3/2011 |
| FR | 2968946 B1 | 4/2013 |
| GB | 816750 | 7/1959 |
| JP | S63156711 A | 6/1988 |
| JP | H06256137 A | 9/1994 |
| JP | 3009959 B2 | 2/2000 |
| JP | 3026213 B2 | 3/2000 |
| JP | 2001-122737 A | 5/2001 |
| JP | 2005145883 A | 6/2005 |
| JP | 2005-194261 A | 7/2005 |
| JP | 3843051 B2 | 11/2006 |

(56) References Cited

FOREIGN PATENT DOCUMENTS

| | | | |
|---|---|---|---|
| JP | 2007-070469 A | 3/2007 | |
| JP | 4329097 B2 | 9/2009 | |
| JP | 4452523 B2 | 4/2010 | |
| JP | 4625357 B2 | 2/2011 | |
| JP | 4679893 B2 | 5/2011 | |
| JP | 4883261 B2 | 2/2012 | |
| JP | 5086539 B2 | 11/2012 | |
| JP | 5228338 B2 | 7/2013 | |
| JP | 2014097931 A | 5/2014 | |
| JP | 5779399 B2 | 9/2015 | |
| WO | 01/28338 A2 | 4/2001 | |
| WO | 01/28339 A2 | 4/2001 | |
| WO | WO 0128339 A2 * | 4/2001 | ............ A01N 43/36 |
| WO | 4329097 B2 | 9/2009 | |
| WO | WO2011074134 A1 | 6/2011 | |
| WO | WO2012131848 A1 | 10/2012 | |
| WO | 2014/002668 A1 | 1/2014 | |
| WO | WO 2014/100970 A1 | 7/2014 | |
| WO | WO2015200778 A1 | 12/2015 | |

OTHER PUBLICATIONS

PCT Invitation to Pay Additional Fees And, Where Applicable, Protest Fee for PCT/US2016/064606 dated Feb. 20, 2017, 14 pages.
PCT Invitation to Pay Additional Fees And, Where Applicable, Protest Fee for PCT/US2016/064604 dated Feb. 15, 2017, 10 pages.
PCT Invitation to Pay Additional Fees And, Where Applicable, Protest Fee for PCT/US2015/064608 dated Feb. 20, 2017, 9 pages.
PCT International Search Report and Written Opinion for PCT/US2016/025827 dated Jun. 24, 2016.
Anonymous: "Spotlight on Apricot Oil, Black Girl with Long Hair", Apr. 5, 2013, Retrieved from the internet: URL: http://blackgirllonghair.com/2013/04/spotlight-on-apricot-oil/, Retrieved Jun. 2, 2016.
PCT International Search Report and Written Opinion for PCT/US2016/064604 dated Apr. 10, 2017.
PCT International Search Report and Written Opinion for PCT/US2016/064606 dated Apr. 12, 2017.
PCT International Search Report and Written Opinion for PCT/US2016/064608 dated Apr. 18, 2017.
"Infusion 23 (Colour) Ologie Leave-in Treatment", Procter & Gamble, Feb. 1, 2007, Mintel.
"Da-Frizz Leave-In Treatment", Quality Collor Cosmeticos, May 1, 2014, Mintel.
PCT Invitation to Pay Additional Fees and, Where Applicabie, Protest Fee for PCT/US2015/036195, dated Oct. 7, 2015.
Invitation to Pay Additional Fees and, Where Applicable, Protest Fee for PCT/US2015/036192 dated Jan. 4, 2016.
Invitation to Pay Additional Fees and, Where Applicable, Protest Fee for PCT/US2015/063893, dated Feb. 8, 2016.
PCT International Search Report and Written Opinion for PCT/US2015/036192 dated Mar. 21, 2016.
PCT Invitation to Pay Additional Fees And, Where Applicable, Protest Fee for PCT/US2015/063888 dated Mar. 9, 2016.
All Final and Non-Final Office Actions for U.S. Appl. No. 14/677,578.
All Final and Non-Final Office Actions for U.S. Appl. No. 14/677,636.
All Final and Non-Final Office Actions for U.S. Appl. No. 14/742,136.
All Final and Non-Final Office Actions for U.S. Appl. No. 14/742,145.
All Final and Non-Final Office Actions for U.S. Appl. No. 14/755,567.
All Final and Non-Final Office Actions for U.S. Appl. No. 14/959,234.
All Final and Non-Final Office Actions for U.S. Appl. No. 14/959,243.
All Final and Non-Final Office Actions for U.S. Appl. No. 15/093,075.
All Final and Non-Final Office Actions for U.S. Appl. No. 15/367,356.
All Final and Non-Final Office Actions for U.S. Appl. No. 15/367,363.
Khan, H., "5 ways to straighten your hair without heat", Flair Beauty Tips, Jul. 12, 2013, pp. 1-4.
Medline Plus "Aging changes in hair and nails", US National Library of Medicine, Oct. 27, 2014, pp. 1-3.
PCT International Search Report and Written Opinion for PCT/US2015/036195 dated Dec. 16, 2015.
U.S. Appl. No. 15/949,539, filed Apr. 10, 2018, Punyani.
U.S. Appl. No. 15/949,555, filed Apr. 10, 2018, Punyani.
Benvenuti, http://www.futurederm.com/what-is-the-best-oil-for-your-hair-argan-oil-vs-pequi-oil-review/, 2011, downloaded Dec. 30, 2018.
All final and non-final office actions for U.S. Appl. No. 15/473,832.
All Final and Non-Final Office Actions for U.S. Appl. No. 15/367,369.
All Final and Non-Final Office Actions for U.S. Appl. No. 15/949,539.
All Final and Non-Final Office Actions for U.S. Appl. No. 15/949,555.
Dow Corning: "Get on the FastTrack to Dry with silicones from Dow Corning", Nov. 19, 2015.
Dow Corning: "Leave-In Conditioner: Fast Dry", Dec. 9, 2015.
Dow Corning: "Revivel Hair Repair Cream: Ideal to Repair Heat Damaged Hair", Jan. 21, 2015.
Dow Corning: "Rinse-Off Conditioner: Fast Dry", Dec. 9, 2015.
John Frieda Frizzease conditioner product (John Frieda, Frizzease smooth start conditioner—https://www.johnfrieda.com/en-UK/products/frizz-ease/smooth-start-conditioner. html, last visit date: Jan. 17, 2018 (year 2018).
Knothe et al., J. Am Oil Chem Soc., 86, pp. 843-856 (2009).
Merriam-Webster Dictionary, obtained online at https://www.merriam-webster.com/dictionary/pH, downloaded on Jun. 29, 2018, pp. 1-14 (2018).
Naturally.com, "Salicylic Acid Shampoo for Curly Hair", pp. 1-3, 2011.
PCT International Search Report and Written Opinion for PCT/US2017/024965 dated Jun. 13, 2017.
Watson, "5 Hair Conditioners You Can Make At Home", retrieved from on-line website: www.wisebread.com, pp. 1-11, 2011.

* cited by examiner

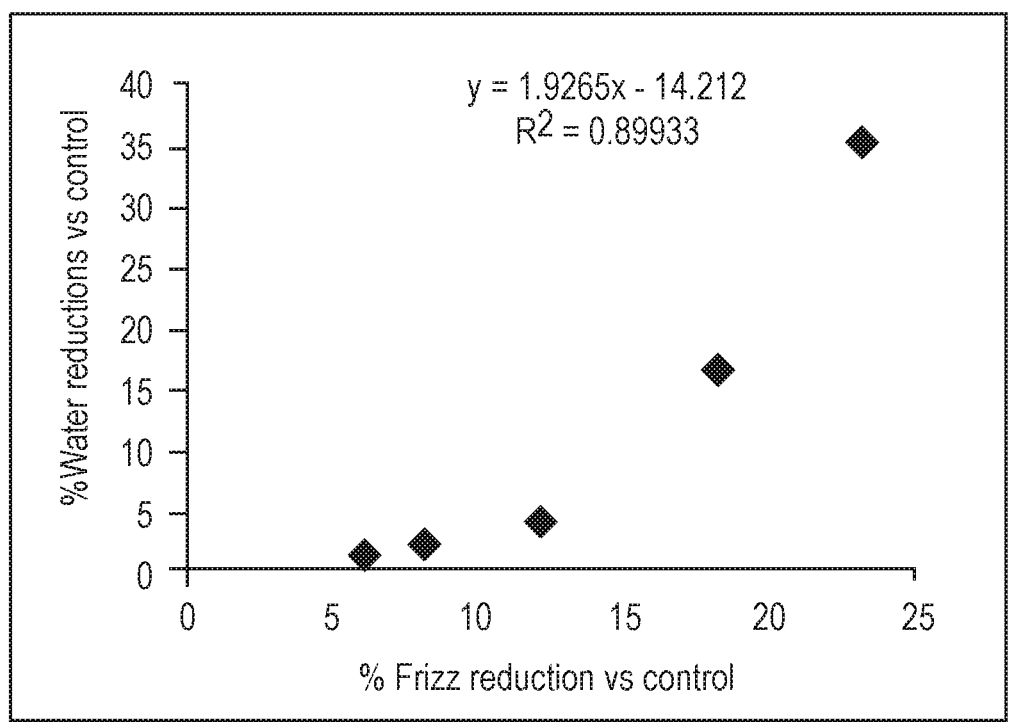

COMPOSITION FOR HAIR FRIZZ REDUCTION

FIELD OF THE INVENTION

The present invention relates to a shampoo composition comprising one or more materials useful for treating hair frizz.

BACKGROUND OF THE INVENTION

Hair frizz is described by consumers as the appearance of unruly fibers at the top of the scalp and tips of hair as well as an increased volume through the bulk of the hair. Generally they see this frizz on days when there is humid weather and the level of moisture in the air is high. The appearance of frizz is undesired and it is often associated with a loss of shine and smoothness. The appearance of frizz and loss of shine and smoothness are associated with a perception of poor hair health. The basic mechanism causing frizz in high humid environments is that at high humidity water penetrates into hair and changes the chemical bond interactions inside the hair. During styling, the consumer will create a 'wet set' where hair is blow dried or flat ironed to create the desired shape. During drying, water is evaporated from hair and hydrogen bonds are formed between the protein peptide chains holding the style in place. As moisture diffuses into hair the hydrogen bonds are broken and hair returns back to its natural shape. For consumers who straighten their hair by blow drying or flat ironing this return to a curled style is associated with a loss of alignment and increased volume. In addition, at high moisture levels in hair the fiber diameter increases which also increases the overall volume of hair.

The typical strategy to prevent frizz is to formulate shampoo products with surface-depositing materials such as silicone, oils, conditioning silicone etc. which make hair more hydrophobic and decrease inter-fiber interactions. At high levels these materials can also provide increased cohesive forces holding fibers together to prevent frizz from occurring. With these materials depositing on the hair surface a greasy look and feel is typically experienced, which is an undesired trade-off of frizz reduction.

Consequently, a need exists for a shampoo product that combines effective frizz control with additional hair benefits that the consumer can notice and feel and, at the same time, is delightful to use without having a sticky or greasy feel.

SUMMARY OF THE INVENTION

In an embodiment, a shampoo composition for hair fizz reduction comprising: from about 0.1% to about 20% of a moisture control material or mixture of moisture control materials wherein the moisture control material is selected from one or more of the following:

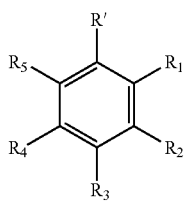

wherein R' is —COOY, sulfonic acid, or C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0;

further wherein and at least about a 4% frizz reduction vs. a control composition without the moisture control material.

Without being bound by theory, the materials in the shampoo treatment composition of the present invention provide excellent frizz performance without a negatively affecting hair feel. These materials prevent water uptake into hair under high humidity conditions, reducing the negative impact of frizz. By providing frizz benefits by penetrating the hair fiber as opposed to depositing on the hair surface, the frizz benefit is not associated by negative hair feel, which is typically observed with current commercial anti-frizz products. These and additional features provided by the embodiments of the present invention will be more fully understood in view of the following detailed description.

BRIEF DESCRIPTION OF THE DRAWINGS

FIG. 1 is graph depicting that there is a monotonic correlation between % water reduction and % frizz reduction.

DETAILED DESCRIPTION OF EMBODIMENTS OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity (RH), unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application" as used in reference to a composition, means to apply or spread the compositions of the present invention onto keratinous fiber such as the hair.

"Dermatologically acceptable" means that the compositions or components described are suitable for use in contact with human skin tissue without undue toxicity, incompatibility, instability, allergic response, and the like.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Safe and effective amount" means an amount of a compound or composition sufficient to significantly induce a positive benefit "Control composition" is a composition that is used for comparison to the inventive composition in terms of performance. Typically, the control composition and the inventive composition are very similar in terms of ingredients and concentrations with the difference being that control composition does not include the material or materials that constitute the invention. Thus, the inventive material(s) that are present in the inventive composition are either substituted by the carrier in the control composition or by a material that is common in the art at the time of the invention.

"Rinse-off" in reference to compositions, means compositions intended to be applied to keratinous substrate and subsequently removed by washing, rinsing or wiping within a few minutes or less from the application. These "rinse-off" compositions are to be distinguished from "leave-on" compositions, which are intended to be applied to and allowed to remain on the keratinous fibers.

The most common hair care rinse-off compositions are shampoos. Shampoos contain detersive surfactants and they are used for cleansing hair, while rinse-off conditioners are typically used after shampoo, they are substantially free of detersive surfactants, they contain conditioning agents to improve hair feel, reverse hair damage and protect against further damage.

"Leave-on," in reference to compositions, means compositions intended to be applied to and allowed to remain on the keratinous fibers. These leave-on compositions are to be distinguished from rinse-off compositions, which are applied to the hair and subsequently (in a few minutes or less) removed either by washing, rinsing, wiping, or the like. Leave-on compositions exclude rinse-off applications such as shampoos, rinse-off shampoos, facial cleansers, hand cleansers, body wash, or body cleansers. The leave-on compositions may be substantially free of cleansing or detersive surfactants. For example, "leave-on compositions" may be left on the keratinous fibers for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Soluble" means at least about 0.1 g of solute dissolves in 100 ml of solvent, at 25° C. and 1 atm of pressure.

All percentages are by weight of the total composition, unless stated otherwise. All ratios are weight ratios, unless specifically stated otherwise. All ranges are inclusive and combinable. The number of significant digits conveys neither a limitation on the indicated amounts nor on the accuracy of the measurements. The term "molecular weight" or "M.Wt." as used herein refers to the weight average molecular weight unless otherwise stated. The weight average molecular weight may be measured by gel permeation chromatography. "QS" means sufficient quantity for 100%.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

Shampoo Composition

The method of reducing fizz described herein comprises applying to the hair a shampoo composition. The shampoo composition delivers consumer desired cleansing and potentially conditioning. It can also deliver frizz reduction in the case that it contains a moisture control material. The shampoo composition may comprise from about 0.1% to about 20% moisture control material selected from the group consisting Class I and Class II materials. After applying to the hair a shampoo composition as described herein, the method then comprises rinsing the shampoo composition from the hair.

Moisture Control Material

The mechanism of action for frizz generation involves moisture from the environment being absorbed by hair and occupying hydrogen bonding sites within hair, including those on the peptide backbone and also associated with acidic and basic side chains of amino acid residues such as lysine, arginine and glutamic acid. This internal water replaces hydrogen bonds that had been created during styling that hold hair in a desired configuration. As a consequence, hair returns to its natural shape which typically leads to unwanted wave, loss of alignment and frizz. In addition, uptake of water by these hydrogen bonding sites swells the hair fiber causing style expansion, which is another indicator of fizz. Without being bound by theory, the materials covered by this invention will replace water at the hydrogen bond sites inside hair and prevent water uptake. Reduction of water inside hair will lead to a reduction in the appearance of frizz under high humidity conditions. Because the mechanism of action is related to the space inside the hair fibers, there are no feel negatives, such as, for example, greasy or oily feel associated with the benefit. The reduction in water uptake is measured using Dynamic Vapor Sorption (DVS) method, which measures a weight increase of hair equilibrated at 90% Relative Humidity (RH) versus 0% RH. Significant frizz benefit is measured on hair treated by materials that caused a reduction in water uptake of higher than 5% versus control hair that is not treated with such materials. The treatment involved the application of a 2% w/w solution of the material in 50:50 water:ethanol solvent.

Preferred materials include salicylic acid, 2,3-dihydroxybenzoic acid, 2,6-dihydroxybenzoic acid, 3-aminobenzoic acid, gallic acid, ethyl gallate, 5-chlorosalicylic acid, trans-ferulic acid, p-coumaric acid, ricinoleic acid, isovaleric acid, isobutyric acid, 2-hexyl-1-decanol, phytol and sorbitan caprylate. These materials are chosen from Molecular Class I and/or Molecular Class II or can also be used in combination to increase the size of the benefit.

In an embodiment of the present invention, the concentration of the Moisture Control Material or the concentration of the mixture of Moisture Control Material in a hair shampoo composition is from about 0.1% to about 20%, in an embodiment from about 0.2% to about 8.0%, and in a further embodiment from about 0.5% to about 5.0%.

Molecular Class I: Polar, Acidic Compounds with the Following Properties:

Protein Binding (PB)>20 AND Molecular Volume (Mol. Vol).<500 AND log P<3 AND Hydrogen-binding (H-binding)>10 AND pKa<5.0, wherein PB is % protein binding, Mol. Vol is molecular volume (in $Å^3$); log P is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name (1% wt/vol) | PB | Mol. Vol. | log P | pKa | H-bond (MPa^½) | % Water Reduction |
|---|---|---|---|---|---|---|
| 2,4-Dihydroxybenzoic acid | 28 | 324 | 1.5 | 3.2 | 23 | 30 |
| 3-Hydroxybenzoic Acid | 38 | 314 | 1.6 | 4.3 | 20 | 20 |
| Gallic acid | 23 | 337 | 0.9 | 4.4 | 23 | 15 |
| 3-Aminobenzoic acid | 41 | 326 | 0.9 | 3.6 | 16 | 12 |
| 4-Aminobenzoic acid | 42 | 323 | 0.9 | 3.5 | 16 | 12 |
| 2,5-Dihydroxybenzoic acid | 31 | 329 | 1.6 | 2.9 | 23 | 27 |
| 3,4-Dihydroxybenzoic acid | 27 | 327 | 0.9 | 4.4 | 23 | 20 |
| 3,5-Dihydroxybenzoic acid | 27 | 327 | 0.9 | 4.1 | 23 | 15 |
| 2,6-Dihydroxybenzoic acid | 37 | 326 | 1.6 | 2.1 | 23 | 35 |
| 5-Chlorosalicylic acid | 56 | 361 | 2.3 | 3.0 | 21 | 28 |
| Salicylic acid | 44 | 320 | 2.1 | 3.1 | 20 | 18 |
| Trans-Ferulic Acid | 50 | 451 | 1.5 | 4.5 | 19 | 6 |
| p-Coumaric acid | 46 | 391 | 1.6 | 4.5 | 20 | 8.8 |
| 4-Hydroxybenzene-sulphonic acid | 55 | 271 | 1.5 | 2.7 | 22 | 26 |
| 3-Chloro-4-hydroxybenzoic acid | 49 | 356 | 2.1 | 4.1 | 20 | 11 |
| 3,5-Dichloro-4-hydroxybenzoic acid | 51 | 397 | 2.8 | 3.8 | 20 | 15 |
| 2,5 Dihydroxy-terephthalic acid | 20 | 375 | 1.1 | 2.1 | 22 | 18 |
| 3-Aminophenol | 45 | 284 | 0.6 | 4 | 17 | 14 |
| 3-Hydroxyanilinium chloride | 32 | 280 | 0.6 | 4 | 17 | 16 |
| 2-Aminophenol | 49 | 288 | 1.0 | 4 | 17 | 14 |
| 4-Aminophenol | 39 | 284 | 0.6 | 4 | 17 | 10 |
| N-4-Hydroxyphenyl-glycine | 37 | 388 | 1.3 | 3 | 13 | 15 | b) Molecular Class II:

Weakly polar to non-polar, weakly to non-acidic compounds that have the following properties: PB>10 AND Mol. Vol.<1500 AND log P>0.5 AND pKa≥5 AND H-binding>4, wherein PB is % protein binding, Mol. Vol is molecular volume (in $Å^3$); log P is n-octanol/water partition coefficients. These properties can be calculated using Volsurf software (http://www.moldiscovery.com/soft_volsurf.php). H-bond is the energy from hydrogen bonds between molecules from Hansen Solubility Parameters and pKa value is a logarithmic measure of the acid dissociation constant.

| Name | PB | Mol. Vol. | logP | pKa | H-bond (MPa^½) | % water reduction |
|---|---|---|---|---|---|---|
| 2-Hydroxyethyl salicylate | 45 | 419 | 1.5 | 8.3 | 19.1 | 10 |
| Ethyl gallate | 43 | 431 | 1.4 | 8.7 | 22.6 | 17 |
| Oleic Acid | 100 | 832 | 7 | 5 | 6.4 | 14 |
| Ricinoleic acid | 84 | 841 | 5.9 | 5 | 17.8 | 8.8 |
| Isovaleric acid | 29 | 295 | 1.3 | 5 | 9.7 | 15 |
| Isobutyric acid | 15 | 254 | 1 | 5 | 10.4 | 5 |
| 2-Hexyl-1-decanol | 87 | 745 | 6.8 | 15 | 10.1 | 11 |
| Phytol | 100 | 874 | 8.0 | 13 | 9.6 | 14 |
| Sorbitan caprylate | 32 | 695 | 1.3 | 12 | 21.8 | 11 |
| Glyceryl monooleate | 96 | 974 | 6.27 | 12.8 | 16.2 | 5 |
| Isostearyl isostearate | 100 | 1527 | 14.7 | 14 | 4.2 | 11 |
| Ethyl linoleate | 82 | 903 | 7.71 | 7.8 | 5.1 | 8 |
| Isopropyl myristate | 97 | 798 | 6.99 | 8.8 | 5.0 | 12 |
| Octyl salicylate | 82 | 646 | 5.4 | 7.1 | 11.7 | 14 |

A Class I having the structure selected from:
1) Class I having the structure selected from:

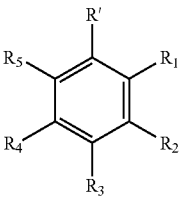

wherein R' is —COOY, sulfonic acid, or —C=CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH=CH—COOR, and wherein the moisture control material is an acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0;

2) Class II having the structure selected from:
a)

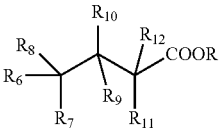

wherein R is hydrogen or metal ion, $R_6$ is methyl, ethyl, propyl, alkenyl or phenyl having less than 12 carbon atoms and wherein $R_7$, $R_8$, $R_9$, $R_{10}$, $R_{11}$, $R_{12}$ are hydrogen, methyl, ethyl, propyl, phenyl, hydroxyl, methoxy or ethoxy groups;

b)

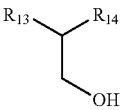

an alcohol wherein R13 is an alkyl, alkenyl, straight or branched carbon chains and; and wherein R14 is hydrogen, hydroxyl, alkyl, methyl, ethyl and propyl wherein the structure of such alcohol contains less than 20 total carbon atoms;

c) An alcohol comprising an unsaturated double bond in the C2 position. A non limiting example would be phytol.

d) an alkyl-substituted glycol wherein the structure of such alkyl substituted glycol contains less than 20 carbon atoms;

e) a monoalkyl or dialkyl substituted glycerin or mono- or di-esters of glycerin with fatty acids wherein the structure of such monoalkyl- or dialkyl-substituted glycerin or glycerin esters contains less than 20 total carbon atoms;

f)

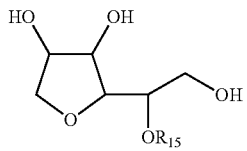

wherein $R_{15}$ could be hydrogen, alkyl, alkenyl, phenyl group and wherein the structure of the $R_{13}$ group contains less than 20 carbon atoms;

g) a fatty acid ester containing from 15-40 total carbon atoms and wherein the moisture control material of Class II is weakly to non-acidic and further wherein the moisture control material of Class II has protein binding higher than 10 and molecular volume lower than 1500 and log P higher than 0.5 and pKa of 5 or higher and hydrogen-binding higher than 4.

Other Components in the Shampoo Composition

A. Detersive Surfactant

The shampoo composition comprises one or more detersive surfactants, which provides cleaning performance to the composition. The one or more detersive surfactants in turn may comprise an anionic surfactant, amphoteric or zwitterionic surfactants, or mixtures thereof. Various examples and descriptions of detersive surfactants are set forth in U.S. Pat. No. 6,649,155; U.S. Patent Application Publication No. 2008/0317698; and U.S. Patent Application Publication No. 2008/0206355, which are incorporated herein by reference in their entirety.

The concentration of the detersive surfactant component in the shampoo composition should be sufficient to provide the desired cleaning and lather performance, and generally ranges from about 2 wt % to about 50 wt %, from about 5 wt % to about 30 wt %, from about 8 wt % to about 25 wt %, from about 10 wt % to about 20 wt %, about 5 wt %, about 10 wt %, about 12 wt %, about 15 wt %, about 17 wt %, about 18 wt %, or about 20 wt %.

Anionic surfactants suitable for use in the compositions are the alkyl and alkyl ether sulfates. Other suitable anionic surfactants are the water-soluble salts of organic, sulfuric acid reaction products. Still other suitable anionic surfactants are the reaction products of fatty acids esterified with isethionic acid and neutralized with sodium hydroxide. Other similar anionic surfactants are described in U.S. Pat. Nos. 2,486,921; 2,486,922; and 2,396,278, which are incorporated herein by reference in their entirety.

Exemplary anionic surfactants for use in the shampoo composition include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. In a further embodiment, the anionic surfactant is sodium lauryl sulfate or sodium laureth sulfate.

Suitable amphoteric or zwitterionic surfactants for use in the shampoo composition herein include those which are known for use in shampoo or other personal care cleansing. Concentrations of such amphoteric surfactants range from about 0.5 wt % to about 20 wt %, and from about 1 wt % to about 10 wt %. Non limiting examples of suitable zwitterionic or amphoteric surfactants are described in U.S. Pat. Nos. 5,104,646 and 5,106,609, which are incorporated herein by reference in their entirety.

Amphoteric detersive surfactants suitable for use in the shampoo composition include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Exemplary amphoteric detersive surfactants for use in the present shampoo composition include cocoamphoacetate, cocoamphodiacetate, lauroamphoacetate, lauroamphodiacetate, and mixtures thereof.

Zwitterionic detersive surfactants suitable for use in the shampoo composition include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. In another embodiment, zwitterionics such as betaines are selected.

Non limiting examples of other anionic, zwitterionic, amphoteric or optional additional surfactants suitable for use in the shampoo composition are described in McCutcheon's, Emulsifiers and Detergents, 1989 Annual, published by M. C. Publishing Co., and U.S. Pat. Nos. 3,929,678, 2,658,072; 2,438,091; 2,528,378, which are incorporated herein by reference in their entirety.

The shampoo composition may also comprise a shampoo gel matrix, an aqueous carrier, and other additional ingredients described herein.

B. Aqueous Carrier

The shampoo composition comprises a first aqueous carrier. Accordingly, the formulations of the shampoo composition can be in the form of pourable liquids (under ambient conditions). Such compositions will therefore typically comprise a first aqueous carrier, which is present at a level of at least 20 wt %, from about 20 wt % to about 95 wt %, or from about 60 wt % to about 85 wt %. The first aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The first aqueous carriers useful in the shampoo composition include water and water solutions of lower alkyl alcohols and polyhydric alcohols. The lower alkyl alcohols useful herein are monohydric alcohols having 1 to 6 carbons, in one aspect, ethanol and isopropanol. The polyhydric alcohols useful herein include propylene glycol, hexylene glycol, glycerin, and propane diol.

C. Shampoo Gel Matrix

In one embodiment, the shampoo composition described herein may comprise a shampoo gel matrix. The shampoo gel matrix comprises (i) from about 0.1% to about 20% of one or more fatty alcohols, alternative from about 0.5% to about 14%, alternatively from about 1% to about 10%, alternatively from about 6% to about 8%, by weight of the shampoo gel matrix; (ii) from about 0.1% to about 10% of one or more shampoo gel matrix surfactants, by weight of the shampoo gel matrix; and (iii) from about 20% to about 95% of an aqueous carrier, alternatively from about 60% to about 85% by weight of the shampoo gel matrix.

The fatty alcohols useful herein are those having from about 10 to about 40 carbon atoms, from about 12 to about 22 carbon atoms, from about 16 to about 22 carbon atoms, or about 16 to about 18 carbon atoms. These fatty alcohols can be straight or branched chain alcohols and can be saturated or unsaturated. Nonlimiting examples of fatty alcohols include, cetyl alcohol, stearyl alcohol, behenyl alcohol, and mixtures thereof. Mixtures of cetyl and stearyl alcohol in a ratio of from about 20:80 to about 80:20 are suitable.

The shampoo gel matrix surfactants may be any of the detersive surfactants described in section "A" herein.

The aqueous carrier may comprise water, or a miscible mixture of water and organic solvent, and in one aspect may comprise water with minimal or no significant concentrations of organic solvent, except as otherwise incidentally incorporated into the composition as minor ingredients of other components.

The aqueous carrier useful herein includes water and water solutions of lower alkyl alcohols and polyhydric alcohols. The lower alkyl alcohols useful herein are monohydric alcohols having 1 to 6 carbons, in one aspect, ethanol and isopropanol. Exemplary polyhydric alcohols useful herein include propylene glycol, hexylene glycol, glycerin, and propane diol.

Additional Components

Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the silicones can be in an emulsified form with droplet size of about 10 nm to about 30 micrometers Other solid or semi-solid conditioning agents may be present in the composition including high melting temperature fatty alcohols, acids, esters, amides or oligomers from unsaturated esters, alcohols, amides. The oligomeric esters may be the result of oligomerization of naturally-occurring unsaturated glyceride esters. Such solid or semi-solid conditioning agents may be added or present as mixtures with organic oils.

Nonionic Polymers

The hair care composition of the present invention may also further comprise a nonionic polymer. According to an embodiment, the conditioning agent for use in the hair care composition of the present invention may include a polyalkylene glycol polymer. For example, polyalkylene glycols having a molecular weight of more than about 1000 are useful herein. Useful are those having the following general formula (VIII):

(VIII)

wherein $R^{11}$ is selected from the group consisting of H, methyl, and mixtures thereof; and v is the number of ethoxy units. The polyalkylene glycols, such as polyethylene glycols, can be included in the hair care compositions of the present invention at a level of from about 0.001 wt. % to about 10 wt. %. In an embodiment, the polyethylene glycol is present in an amount up to about 5 wt. % based on the weight of the composition. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

Organic Conditioning Materials

The conditioning agent of the compositions of the present invention may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) fatty alcohols, vi) alkyl glucosides and alkyl glucoside derivatives; vii) quaternary ammonium compounds; viii) polyethylene glycols and polypropylene glycols having a molecular weight of up to about 2,000,000 including those with CTFA names PEG-200, PEG-400, PEG-600, PEG-1000, PEG-2M, PEG-7M, PEG-14M, PEG-45M and mixtures thereof.

Deposition Aids

The hair care compositions of the present invention may further comprise a deposition aid, such as a cationic polymer. Cationic polymers useful herein are those having an average molecular weight of at least about 5,000, alternatively from about 10,000 to about 10 million, and alternatively from about 100,000 to about 2 million.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. Other suitable spacer monomers include vinyl esters, vinyl alcohol (made by hydrolysis of polyvinyl acetate), maleic anhydride, propylene glycol, and ethylene glycol. Other suitable cationic polymers useful herein include, for example, cationic celluloses, cationic starches, and cationic guar gums.

The cationic polymer can be included in the hair care compositions of the present invention at a level of from about 0.001 wt. % to about 10 wt. %. In one embodiment, the cationic polymer is present in an amount up to about 5 wt % based on the weight of the composition.

Benefit Agents

In an embodiment, the hair care composition further comprises one or more additional benefit agents. The benefit agents comprise a material selected from the group consisting of anti-dandruff agents, anti-fungal agents, anti-itch agents, anti-bacterial agents, anti-microbial agents, moisturization agents, anti-oxidants, vitamins, lipid soluble vitamins, chelants, perfumes, brighteners, enzymes, sensates, attractants, dyes, pigments, bleaches, and mixtures thereof. In one aspect said benefit agent may comprise an anti-dandruff agent. Such anti-dandruff particulate should be physically and chemically compatible with the components of the composition, and should not otherwise unduly impair product stability, aesthetics or performance.

According to an embodiment, the hair care composition comprises an anti-dandruff active, which may be an anti-dandruff active particulate. In an embodiment, the anti-dandruff active is selected from the group consisting of: pyridinethione salts; azoles, such as ketoconazole, econazole, and elubiol; selenium sulphide; particulate sulfur; keratolytic agents such as salicylic acid; and mixtures thereof. In an embodiment, the anti-dandruff particulate is a pyridinethione salt. Pyridinethione particulates are suitable particulate anti-dandruff actives. In an embodiment, the anti-dandruff active is a 1-hydroxy-2-pyridinethione salt and is in particulate form. In an embodiment, the concentration of pyridinethione anti-dandruff particulate ranges from about 0.01 wt. % to about 5 wt. %, or from about 0.1 wt. % to about 3 wt. %, or from about 0.1 wt. % to about 2 wt. %. In an embodiment, the pyridinethione salts are those formed from heavy metals such as zinc, tin, cadmium, magnesium, aluminium and zirconium, generally zinc, typically the zinc salt of 1-hydroxy-2-pyridinethione (known as "zinc pyridinethione" or "ZPT"), commonly 1-hydroxy-2-pyridinethione salts in platelet particle form. In an embodiment, the 1-hydroxy-2-pyridinethione salts in platelet particle form have an average particle size of up to about 20 microns, or up to about 5 microns, or up to about 2.5 microns. Salts formed from other cations, such as sodium, may also be suitable. Pyridinethione anti-dandruff actives are described, for example, in U.S. Pat. Nos. 2,809,971; 3,236,733; 3,753, 196; 3,761,418; 4,345,080; 4,323,683; 4,379,753; and 4,470,982.

In an embodiment, in addition to the anti-dandruff active selected from polyvalent metal salts of pyrithione, the composition further comprises one or more anti-fungal and/or anti-microbial actives. In an embodiment, the anti-microbial active is selected from the group consisting of: coal tar, sulfur, charcoal, whitfield's ointment, castellani's paint, aluminum chloride, gentian violet, octopirox (piroctone olamine), ciclopirox olamine, undecylenic acid and its metal salts, potassium permanganate, selenium sulphide, sodium thiosulfate, propylene glycol, oil of bitter orange, urea preparations, griseofulvin, 8-hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, Sensiva SC-50, Elestab HP-100, azelaic acid, lyticase, iodopropynyl butylcarbamate (IPBC), isothiazalinones such as octyl isothiazalinone, and azoles, and mixtures thereof. In an embodiment, the anti-microbial is selected from the group consisting of: itraconazole, ketoconazole, selenium sulphide, coal tar, and mixtures thereof.

In an embodiment, the azole anti-microbials is an imidazole selected from the group consisting of: benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and mixtures thereof, or the azole anti-microbials is a triazole selected from the group consisting of: terconazole, itraconazole, and mixtures thereof. When present in the hair care composition, the azole anti-microbial active is included in an amount of from about 0.01 wt. % to about 5 wt. %, or from about 0.1 wt. % to about 3 wt. %, or from about 0.3 wt. % to about 2 wt. %. In an embodiment, the azole anti-microbial active is ketoconazole. In an embodiment, the sole anti-microbial active is ketoconazole.

Embodiments of the hair care composition may also comprise a combination of anti-microbial actives. In an embodiment, the combination of anti-microbial active is selected from the group of combinations consisting of: octopirox and zinc pyrithione, pine tar and sulfur, salicylic acid and zinc pyrithione, salicylic acid and elubiol, zinc pyrithione and elubiol, zinc pyrithione and climbasole, octopirox and climbasole, salicylic acid and octopirox, and mixtures thereof.

In an embodiment, the composition comprises an effective amount of a zinc-containing layered material. In an embodiment, the composition comprises from about 0.001 wt. % to about 10 wt. %, or from about 0.01 wt. % to about 7 wt. %, or from about 0.1 wt. % to about 5 wt. % of a zinc-containing layered material, by total weight of the composition.

Zinc-containing layered materials may be those with crystal growth primarily occurring in two dimensions. It is conventional to describe layer structures as not only those in which all the atoms are incorporated in well-defined layers, but also those in which there are ions or molecules between the layers, called gallery ions (A. F. Wells "Structural Inorganic Chemistry" Clarendon Press, 1975). Zinc-containing layered materials (ZLMs) may have zinc incorporated in the layers and/or be components of the gallery ions. The following classes of ZLMs represent relatively common examples of the general category and are not intended to be limiting as to the broader scope of materials which fit this definition.

Many ZLMs occur naturally as minerals. In an embodiment, the ZLM is selected from the group consisting of: hydrozincite (zinc carbonate hydroxide), aurichalcite (zinc copper carbonate hydroxide), rosasite (copper zinc carbonate hydroxide), and mixtures thereof. Related minerals that are zinc-containing may also be included in the composition. Natural ZLMs can also occur wherein anionic layer species such as clay-type minerals (e.g., phyllosilicates) contain ion-exchanged zinc gallery ions. All of these natural materials can also be obtained synthetically or formed in situ in a composition or during a production process.

Another common class of ZLMs, which are often, but not always, synthetic, is layered double hydroxides. In an embodiment, the ZLM is a layered double hydroxide conforming to the formula $[M^{2+}_{1-x}M^{3+}_x(OH)_2]^{x+}A^{m-}_{x/m} \cdot nH_2O$ wherein some or all of the divalent ions ($M^{2+}$) are zinc ions (Crepaldi, E L, Pava, P C, Tronto, J, Valim, J B *J. Colloid Interfac. Sci.* 2002, 248, 429-42). Yet another class of ZLMs can be prepared called hydroxy double salts (Morioka, H., Tagaya, H., Karasu, M, Kadokawa, J, Chiba, K *Inorg. Chem.* 1999, 38, 4211-6). In an embodiment, the ZLM is a hydroxy double salt conforming to the formula $[M^{2+}_{1-x}M^{2+}_{1+x}(OH)_{3(1-y)}]^{+}$ $A^{n-}_{(1=3y)/n}.nH_2O$ where the two metal ions ($M^{2+}$) may be the same or different. If they are the same and represented by zinc, the formula simplifies to $[Zn_{1+x}(OH)_2]^{2x+}2xA^{-}.nH_2O$. This latter formula represents (where x=0.4) materials such as zinc hydroxychloride and zinc hydroxynitrate. In an embodiment, the ZLM is zinc hydroxychloride and/or zinc hydroxynitrate. These are related to hydrozincite as well wherein a divalent anion replace the monovalent anion. These materials can also be formed in situ in a composition or in or during a production process.

In embodiments having a zinc-containing layered material and a pyrithione or polyvalent metal salt of pyrithione, the ratio of zinc-containing layered material to pyrithione or a polyvalent metal salt of pyrithione is from about 5:100 to about 10:1, or from about 2:10 to about 5:1, or from about 1:2 to about 3:1.

The on-scalp deposition of the anti-dandruff active is at least about 1 microgram/cm$^2$. The on-scalp deposition of the anti-dandruff active is important in view of ensuring that the anti-dandruff active reaches the scalp where it is able to perform its function. In an embodiment, the deposition of the anti-dandruff active on the scalp is at least about 1.5 microgram/cm$^2$, or at least about 2.5 microgram/cm$^2$, or at least about 3 microgram/cm$^2$, or at least about 4 microgram/cm$^2$, or at least about 6 microgram/cm$^2$, or at least about 7 microgram/cm$^2$, or at least about 8 microgram/cm$^2$, or at least about 8 microgram/cm$^2$, or at least about 10 microgram/cm$^2$. The on-scalp deposition of the anti-dandruff active is measured by having the hair of individuals washed with a composition comprising an anti-dandruff active, for example a composition pursuant to the present invention, by trained a cosmetician according to a conventional washing protocol. The hair is then parted on an area of the scalp to allow an open-ended glass cylinder to be held on the surface while an aliquot of an extraction solution is added and agitated prior to recovery and analytical determination of anti-dandruff active content by conventional methodology, such as HPLC.

Carrier

The composition of the present invention may comprise an aqueous carrier. The level and species of the carrier are selected according to the compatibility with other components, and other desired characteristic of the product.

The carrier useful in the present invention includes water and water solutions of lower alkyl alcohols. The lower alkyl alcohols useful herein are monohydric alcohols having 1 to 6 carbons, and in a further embodiment, ethanol and isopropanol.

In an embodiment of the present invention, the aqueous carrier is substantially water. In a further embodiment, deionized water may be used. Water from natural sources including mineral cations can also be used, depending on the desired characteristic of the product. Generally, the compositions of the present invention comprise from about 0% to about 99%, in an embodiment from about 50% to about 95%, in a further embodiment from about 70% to about 90%, and in a further embodiment from about 80% to about 90% water.

Rheology Modifier/Suspending Agents

In one embodiment, the rinse-off shampoo composition comprises a rheology modifier. The rheology modifier increases the substantivity and stability of the composition, improve feel and consumer's use experience (e.g. non-dripping, spreadability, etc). Any suitable rheology modifier can be used. In an embodiment, the hair care composition may comprise from about 0.05% to about 10% of a rheology modifier, in a further embodiment, from about 0.1% to about 10% of a rheology modifier, in yet a further embodiment, from about 0.5% to about 2% of a rheology modifier, in a further embodiment, from about 0.7% to about 2% of a rheology modifier, and in a further embodiment from about 1% to about 1.5% of a rheology modifier. In an embodiment, the rheology modifier may be a polyacrylamide thickener. In an embodiment, the rheology modifier may be a polymeric rheology modifier.

In one embodiment, the rinse-off shampoo composition may comprise rheology modifiers that are homopolymers based on acrylic acid, methacrylic acid or other related derivatives, non-limiting examples include polyacrylate, polymethacrylate, polyethylacrylate, and polyacrylamide.

In another embodiment, the rheology modifiers may be alkali swellable and hydrophobically-modified alkali swellable acrylic copolymers or methacrylate copolymers non-limiting examples include acrylic acid/acrylonitrogen copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/vinylneodecanoate crosspolymer, and acrylates/C10-C30 alkyl acrylate crosspolymer.

In a further embodiment, the rheology modifiers may be crosslinked acrylic polymers, a non-limiting example includes carbomers.

In a father embodiment, the rheology modifiers may be alginic acid-based materials; non-limiting examples include sodium alginate, and alginic acid propylene glycol esters.

In a further embodiment, the rheology modifier may be an associative polymeric thickeners, non-limiting examples include: Hydrophobically modified cellulose derivatives; Hydrophobically modified alkoxylated urethane polymers, nonlimiting example include PEG-150/decyl alcohol/SMDI copolymer, PEG-150/stearyl alcohol/SMDI copolymer, polyurethane-39; Hydrophobically modified, alkali swellable emulsions, non-limiting examples include hydrophobically modified polyacrylates, hydrophobically modified polyacrylic acids, and hydrophobically modified polyacrylamides; hydrophobically modified polyethers wherein these materials may have a hydrophobe that can be selected from cetyl, stearyl, oleayl, and combinations thereof, and a hydrophilic portion of repeating ethylene oxide groups with repeat units from 10-300, in another embodiment from 30-200, in a further embodiment from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

In a further embodiment, the rheology modifier may be cellulose and derivatives; nonlimiting examples include microcrystalline cellulose, carboxymethylcelluloses, hydroxyethylcellulose, hydroxypropylcellulose, hydroxypropylmethylcellulose, methylcellulose, ethylcellulose, nitro cellulose, cellulose sulfate, cellulose powder, and hydrophobically modified celluloses In an embodiment, the rheology modifier may be a guar and guar derivatives; nonlimiting examples include hydroxypropyl guar, and hydroxypropyl guar hydroxypropyl trimonium chloride.

In an embodiment, the rheology modifier may be polyethylene oxide, polypropylene oxide, and POE-PPO copolymers.

In an embodiment, the rheology modifier may be polyvinylpyrrolidone, crosslinked polyvinylpyrrolidone and derivatives. In a further embodiment, the rheology modifier may be polyvinylalcohol and derivatives.

In a further embodiment, the rheology modifier may be polyethyleneimine and derivatives.

In another embodiment, the rheology modifier may be silicas; nonlimiting examples include fumed silica, precipitated silica, and silicone-surface treated silica.

In an embodiment, the rheology modifier may be waterswellable clays non-limiting examples include laponite, bentolite, montmorilonite, smectite, and hectonite.

In an embodiment, the rheology modifier may be gums nonlimiting examples include xanthan gum, guar gum, hydroxypropyl guar gum, Arabia gum, tragacanth, galactan, carob gum, karaya gum, and locust bean gum.

In a further embodiment, the rheology modifier may be, dibenzylidene sorbitol, karaggenan, pectin, agar, quince seed (*Cydonia oblonga* Mill), starch (from rice, corn, potato, wheat, etc), starch-derivatives (e.g. carboxymethyl starch, methylhydroxypropyl starch), algae extracts, dextran, succinoglucan, and pulleran.

In an embodiment, the composition of the present invention may comprise suspending agents including crystalline suspending agents which can be categorized as acyl derivatives, long chain amine oxides, and mixtures thereof. These suspending agents are described in U.S. Pat. No. 4,741,855. These suspending agents include ethylene glycol esters of fatty acids in one aspect having from about 16 to about 22 carbon atoms. In one aspect, useful suspending agents include ethylene glycol stearates, both mono and distearate, but in one aspect, the distearate containing less than about 7% of the mono stearate. Other suitable suspending agents include alkanol amides of fatty acids, having from about 16 to about 22 carbon atoms, or even about 16 to 18 carbon atoms, examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin® R available from Rheox, Inc. Long chain acyl derivatives, ethylene glycol esters of long chain carboxylic acids, long chain amine oxides, and alkanol amides of long chain carboxylic acids in addition to the materials listed above may be used as suspending agents. Other long chain acyl derivatives suitable for use as suspending agents include N,N-dihydrocarbyl amido benzoic acid and soluble salts thereof (e.g., Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl dimethyl amine oxides, e.g., stearyl dimethyl amine oxide. Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Non-limiting examples of rheology modifiers include acrylamide/ammonium acrylate copolymer (and)polyisobutene (and) polysorbate 20, acrylamide/sodium acryloyldimethyl taurate copolymer/isohexadecane/polysorbate 80, acrylates copolymer; acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil, C12-16 alkyl PEG-2 hydroxypropylhydroxyethyl ethylcellulose (HM-EHEC), carbomer, crosslinked polyvinylpyrrolidone (PVP), dibenzylidene sorbitol, hydroxyethyl ethylcellulose (EHEC), hydroxypropyl methylcellulose (HPMC), hydroxypropyl methylcellulose (HPMC), hydroxypropylcellulose (HPC), methylcellulose (MC), methylhydroxyethyl cellulose (MEHEC), PEG-150/decyl alcohol/SMDI copolymer, PEG-150/stearyl alcohol/SMDI copolymer, polyacrylamide/C13-14 isoparaffin/laureth-7; polyacrylate 13/polyisobutene/polysorbate 20; polyacrylate crosspolymer-6, polyamide-3; polyquaternium-37 (and) hydrogenated polydecene (and) trideceth-6, polyurethane-39, sodium acrylate/acryloyldimethyltaurate/dimethylacrylamide, crosspolymer (and) isohexadecane (and) polysorbate 60; sodium polyacrylate. Exemplary commercially-available rheology modifiers include ACULYN™ 28, Klucel™ M CS, Klucel™ H CS, Klucel™ G CS, SYLVACLEAR™ AF1900V, SYLVACLEAR™ PA1200V, Benecel™ E10M, Benecel™ K35M, Optasense™ RMC70, ACULYN™33, ACULYN™46, ACULYN™22, ACULYN™44, Carbopol Ultrez™ 20, Carbopol Ultrez™ 21, Carbopol Ultrez™ 10, Carbopol Ulterez™ 30, Carbopol™ 1342, Carbopol™ 934, Carbopol™ 940, Carbopol™ 950, Carbopol™ 980, and Carbopol™ 981, Acrysol™ 22, Sepigel™ 305, Simulgel™600, Sepimax Zen, Simulquat HC 305 and combinations thereof.

pH of Compositions

Below is the data of the difference of % water reduction of hair treated with leave on composition containing 1% salicylic acid in ethanol:water (50:50) at various values of pH vs control (hair treated with composition of ethanol:water (50:50). As shown in below table, at lower pH, the present invention demonstrates improved performance compared to higher pH.

| Raw Material | Formula Example | | | |
| --- | --- | --- | --- | --- |
| | pH 3 | pH 4.2 | pH 7 | pH 10 |
| Distilled Water | QS | QS | QS | QS |
| Ethanol | 50.0 | 50.0 | 50.0 | 50.0 |
| Salicylic acid | 1.0 | 1.0 | 1.0 | 1.0 |
| Final pH | 3.2 | 4.2 | 7 | 10 |
| % Water Reduction | 30 | 27 | 22 | 15 |

In an embodiment of the present invention, the pH of a composition of the present invention comprising material from Molecular Class I may be in the range of from about 1 to about 9, in another embodiment a pH of from about 2 to about 7, in a further embodiment a pH of from about 4 to about 5.5.

In an embodiment of the present invention, the Moisture control Material is a carboxylic acid ester. In an embodiment, the carboxylic acid ester is based on a fatty acid wherein the molecule of the fatty acid comprises of more than 14 carbon atoms. Non-limiting examples of such esters are isostearyl isostearate, methyl stearate, methyl palmitate, and methyl oleate. In another embodiment of the present invention, the carboxylic acid ester is part of a mixture of materials prepared via the reaction of natural oils using methanol. Non-limiting examples of such mixture is the mixture that is produced by the product of the reaction of refined palm kernel oil with methanol, followed by fractionation via distillation. A commercial product that meets this description is the Heavy Cut Ester CE-1875 (supplied by P&G Chemicals with CAS Number 6772-38-3) containing ingredients such as methyl stearate, methyl palmitate, methyl oleate as major ingredients, as well as methyl laurate, methyl myristate, methyl behenate and other materials as minor ingredients.

FORMULATIONS AND EXAMPLES

The following are non-limiting examples of the present invention. The examples are given solely for the purpose of illustration and are not to be construed as limitations of the present invention, as many variations thereof are possible without departing from the spirit and scope of the invention, which would be recognized by one of ordinary skill in the art.

Examples

Shampoo Composition Preparation:

The shampoo composition delivers consumer desired shampooing in addition to preventing water uptake inside the hair at high humidity.

The shampoo composition comprises from about 0.2% to about 10%, alternatively from about 1% to about 7%, alternatively from about 2% to about 5% of a compound selected from the group consisting of Moisture Control Material Molecular Class I e.g. Salicylic acid, 2, 4 dihydroxybenzoic acid etc. and/or Moisture Control Material Molecular Class II e.g. 2-hexyldecanol, Isostearyl Isostearate etc. and mixtures thereof, by weight of the shampoo composition. After applying to the hair a shampoo composition as described herein, the method then comprises rinsing the shampoo composition from the hair.

Shampoo Hair Treatment Protocol:

All testing are performed on Virgin Caucasian Hair weighing approximately 2.0 grams and having a length of approximately 6 inches for Dynamic Vapor Sorption measurement and Caucasian Damaged Frizzy hair switches weighing approximately 4.0 grams and having a length of approximately 6 inches for Frizz Reduction. The hair switches are commercially available from IHIP (International Hair Importers). Three hair switches per rinse-off compositions per dosage are used. Each hair switch is pre-washed with clarifying shampoo and allowed to dry. An amount of 0.40 g of the shampoo composition is spread via a syringe onto the separate pre-washed hair switch. That is, the dosage is 0.20 g of shampoo per g of hair. Each application consists of adding shampoo to the hair, milking for 30 seconds followed by rinsing for 30 seconds. Excess water is squeezed from the hair switches and blow dried. This protocol is repeated for 5 times/cycles.

Evaluation Methods

The hair switches that are treated with the shampoo compositions are evaluated using the following methodologies.

a. DVS Measurement

After the hair is exposed to the shampoo treatment, it is blow-dried and analyzed for water absorption-desorption as a function of Relative Humidity (RH) according to the following procedure using Dynamic Vapor Sorption (DVS) method. More specifically, the hair switch is weighed and hold for equilibration at 0% RH for 16 hours. After the 16-hour period, the RH is increased to 10% and maintained at this level for 6 hours. Then, the RH is increased by 10% after every 6 hours interval until it reaches 90% RH. The % water reduction is calculated as follows:

A=Amount of water absorbed at 90% RH by the hair treated with composition containing the Moisture Control Material
B=Amount of water absorbed at 90% RH by the hair treated with control composition (only carrier) containing no Moisture Control Material $$\% \text{ Water reduction} = [(B-A) \times 100]/B$$

The standard error for DVS measurement is less than 0.05
Active Penetration Inside Hair 0.1 g-0.2 g of hair are added to 10.0 mL of Extraction Solvent A i.e. Acetone with 0.1% TFA (Trifluoroacetic acid) for 15 min. Add an additional 5.0 mL of Extraction Solvent A to the vial with the hair for another 15 min. The extract is transferred into the same vial containing the first extract. This sample is for determining the surface 5-chlorosalicylic acid or salicylic acid. Add 10.0 mL of Extraction Solvent B i.e pH 10 Ammonia buffer:MeOH (90:10), kept for overnight (for at least 18 h). This sample is for determining the internal 5-chlorosalicylic acid or salicylic acid.

b. Determination of Frizz Reduction

The hair switches are thoroughly blow-dried after the treatment with shampoo while holding the hair switch with all the hair fibers at the tip and then the hair switches are heat straightened by sectioning the hair into three parts and then heat with flat iron for 8 passes at 400-450 F. Hair switches are then kept at low humidity (between 20-25% RH) for equilibration for at least an hour. After the equilibration period, the hair switches are transferred to high humidity chamber (85-90% RH) for frizz assessment. Image of hair switches using a NIR Camera with parallel polarizers and are taken immediately after insertion of the hair into the high humidity chamber (to). Another image is taken after 3 hours ($t_{3h}$). The pixels are analyzed (selecting the entire hair switch) for 2D projection of volume (using vncviewer software). Then, the mean projected area is determined for the hair switch at $t_0$ ($A_{t0}$) and for the hair at $t_{3h}$ ($A_{t3h}$) and the frizz calculated using the equation given below. Each experiment is repeated with 3 hair switches. The percentFrizz is calculated using below equation:

$$\% \text{ Frizz} = 100 \times (A_{t3h} - A_{t0}/A_{t0})$$

$$\% \text{ Frizz reduction} = 100 \times (\% \text{ Frizz(present invention composition)} - \% \text{ Frizz(control composition}/\% \text{ Frizz(control composition)}.$$

The standard error for Frizz measurement is less than 0.1
Correlation of % Frizz Reduction Vs % Water Reduction Determined by DVS Methodology Results obtained from DVS measurements and the results from the determination of the frizz reduction methodology of various switches indicate that there is a correlation between the two methods. In other words, hair switches that show low water reduction also show % higher frizz reduction as shown in FIG. 1.

FIG. 1 depicting correlation of % water reduction vs % frizz reduction, where hair switches with different dosage are treated and their % water reduction and % frizz reduction is measured using DVS and frizz method respectively.

FIG. 1 is a plot depicting that there is a monotonic correlation between % water reduction and % frizz reduction. As material dosage increases, % water reduction increase resulting in increase in % frizz reduction i.e. more frizz control.

Results

As FIG. 1 demonstrates, there is a monotonic correlation between % water reduction and % frizz reduction. As material dosage increases, more material penetrates into hair, The % water reduction at high humidity increases resulting in an increase in % frizz reduction i.e. more frizz control. This confirms the present invention's technical hypothesis of material penetration, interaction with hair protein and decrease of water uptake inside hair at high humidity resulting in frizz control.

Shampoo Formulation and % Water Reduction:

| | Shampoo Formula Example | | | | | | | | |
|---|---|---|---|---|---|---|---|---|---|
| | Control A | B | C | D | E | F | G | H | I |
| Raw Material | (wt./wt.) % | (wt./wt.) % | (wt./wt.) % | (wt./wt.) % | (wt./wt.) % | (wt./wt.) % | (wt./wt.) % | (wt./wt.) % | (wt./wt.) % |
| Water Purified | Q.S to 100 | Q.S to 100 | Q.S to 100 | Q.S to 100 | Q.S to 100 | Q.S to 100 | Q.S to 100 | Q.S to 100 | Q.S to 100 |
| Sodium Laureth 3 Sulfate 28% solution | 21.6 | 21.6 | 21.6 | 21.6 | 21.6 | 21.6 | 21.6 | 21.6 | 21.6 |
| Sodium Lauryl Sulfate 29% solution | 34.5 | 34.5 | 34.5 | 34.5 | 34.5 | 34.5 | 34.5 | 34.5 | 34.5 |
| Laureth-4 | 0.9 | 0.9 | 0.9 | 0.9 | 0.9 | 0.9 | 0.9 | 0.9 | 0.9 |
| Dimethicone 330M cps | 0.5 | 0.5 | 0.5 | 0.5 | 0.5 | 0.5 | 0.5 | 0.5 | 0.5 |
| Glycol Distearate | 1.5 | 1.5 | 1.5 | 1.5 | 1.5 | 1.5 | 1.5 | 1.5 | 1.5 |
| Polyquaternium-6 | 0.32 | 0.32 | 0.32 | 0.32 | 0.32 | 0.32 | 0.32 | 0.32 | 0.32 |
| Sodium Benzoate | 0.27 | 0.27 | 0.27 | 0.27 | 0.27 | 0.27 | 0.27 | 0.27 | 0.27 |
| Citric acid 50% Solution | 0.52 | 0.52 | 0.52 | 0.52 | 0.52 | 0.52 | 0.52 | 0.52 | 0.52 |
| Methylchloro-isothiazolinone/ methyliso-thiazolinone | 0.035 | 0.035 | 0.035 | 0.035 | 0.035 | 0.035 | 0.035 | 0.035 | 0.035 |
| Sodium chloride | 1.66 | 1.66 | 1.66 | 1.66 | 1.66 | 1.66 | 1.66 | 1.66 | 1.66 |
| Fragrance | 0.65 | 0.65 | 0.65 | 0.65 | 0.65 | 0.65 | 0.65 | 0.65 | 0.65 |
| DL-Panthenol 56% solution | 0.05 | 0.05 | 0.05 | 0.05 | 0.05 | 0.05 | 0.05 | 0.05 | 0.05 |
| Panthenyl Ethyl ether | 0.03 | 0.03 | 0.03 | 0.03 | 0.03 | 0.03 | 0.03 | 0.03 | 0.03 |
| Glycol Distearate | 1.5 | 1.5 | 1.5 | 1.5 | 1.5 | 1.5 | 1.5 | 1.5 | 1.5 |
| Salicylic acid[1] | 0 | 1.0 | 0.0 | 0.0 | 0.0 | 0.0 | 0 | 1 | 1 |
| 5-Chloro Salicylic acid[2] | 0 | 0 | 1.0 | 0 | 0 | 0 | 0 | 0 | 0 |
| 2,4 dihydroxy-benzoic acid[3] | 0 | 0 | 0 | 1 | 0 | 0 | 0 | 0.15 | 0 |
| Isostearyl Isostearate[4] | 0 | 0 | 0 | 0 | 1 | 0 | 0 | 1 | 1 |
| 2-hexyl-decanol[5] | 0 | 0 | 0 | 0 | 0 | 1 | 0 | 5 | 5 |
| Oleic acid[6] | 0 | 0 | 0 | 0 | 0 | 0 | 0.2 | 0 | 0.2 |
| % Water Reduction versus Control at dose of 0.2 g of composition for 1 g of hair | — | 0.6 | 0.8 | 0.3 | 0.4 | 0.6 | 0.1 | 1.2 | 2 |

[1]Supplied by API Corpotration
[2]Supplied by Sigma Aldrich
[3]Supplied by Sigma Aldrich
[4]Crodamol ISIS supplied by Croda
[5]Isofol 16 supplied by Sasol (Brunsbuettel, DE)
[6]Greenolene 6928 supplied by Green Oleo Results:

Formula B to I showed % water reduction at high humidity. The addition of two or more moisture control materials to shampoo formulation shows higher % water reduction than one moisture control material.

Shampoo Formulations, Salicylic Acid Penetration and % Water Reduction:

|  | J | K | L | M |
|---|---|---|---|---|
| Sodium laureth-1 sulfate | 14.9 | 14.9 | 14.9 | 14.9 |
| Guar hydroxypropyltrimonium chloride | 0.33 | 0.33 | 0.33 | 0.33 |
| Polyquaternium-10 | 0.078 | 0.078 | 0.078 | 0.078 |
| Sodium chloride | 0.69 | 0.69 | — | — |
| Salicylic acid | 2.0 | 2.0 | 2.0 | 2.0 |
| Isostearyl isosterate | — | 1.0 | — | — |
| 2-hexyl decanol | — | 5.0 | — | — |
| Tetrasodium EDTA tetrathydrate | 0.16 | 0.16 | 0.16 | 0.16 |
| Sodium benzoate | 0.25 | 0.25 | 0.25 | 0.25 |
| Glycerin | 0.50 | 0.50 | 0.50 | 0.50 |
| Dimethiconol and Dimethicone | 1.90 | 1.90 | 1.90 | — |
| Sodium xylenesulfonate | — | 0.42 | 0.42 | 0.87 |
| Polyquaternium-6 | 0.08 | 0.08 | 0.08 | 0.08 |
| Trihydroxystearin | 0.06 | 0.06 | 0.06 | 0.06 |
| Sodium lauryl sulfate | 3.93 | 3.93 | 3.93 | — |
| Methylchoroisothiazolinone/methlisothi | 0.035 | 0.035 | 0.035 | 0.035 |
| Stearyl alcohol | 1.16 | 1.16 | 1.16 | — |
| Cetyl alcohol | 0.64 | 0.64 | 0.64 | — |
| Cocamidopropyl Betaine | 1.70 | 1.70 | 1.70 | 1.70 |
| Perfume | 0.90 | 0.90 | 0.90 | 0.90 |
| Water | Balance | Balance | Balance | Balance |
| Adjust pH (NaOH or Citric acid) | 6.0 | 6.0 | 4.0 | 4.0 |

|  | N | O |
|---|---|---|
| Sodium lauryl sulfate | 9.5 | 9.5 |
| Sodium laureth-3 sulfate | 6.0 | 6.0 |
| Methocel E50 | 0.25 | 0.25 |
| Salicylic acid | 2.0 | — |
| Tetrasodium EDTA tetrathydrate | 0.16 | 0.16 |
| Sodium benzoate | 0.25 | 0.25 |
| Cocamidopropyl Betaine | 5.0 | 5.0 |
| Sodium xylenesulfonate | 0.21 | 0.21 |
| Ethylene Diamine Disuccinic Acid Trisodium Salt | 0.26 | 0.26 |
| Kathon | 0.0033 | 0.0033 |
| Perfume | 0.65 | 0.65 |
| Water | Balance | Balance |
| Adjust pH using NaOH or Citric acid | 4.1 | 5.9 |

Results table below shows ppm of salicylic acid (SA) penetration into hair.
1. Salicylic acid (SA) penetration (ppm) inside hair. pH of the shampoo formulation has been demonstrated to have an effect for salicylic acid penetration. It is shown that in all the pH 4 formulas SA penetration inside hair increased as the number of uses increase, i.e., SA is accumulating inside hair every time the shampoo is used. This is in contrast to the pH 6 formulas, while the amount of penetrated is higher than the pH 4 formulas after one shampoo, SA is not accumulated after multiple uses.

|  | ppm of salicylic acid | | | | | |
|---|---|---|---|---|---|---|
|  | Sample J pH 6.0 | Formula K pH 6.0 | Formula L pH 4.0 | Formula M pH 4.0 | Formula N pH 4.0 | Formula O pH 6.0 |
| % SA in formula | 2.0 | 2.0 | 2.0 | 2.0 | 2.0 | 0.0 |
| 1× shampoo | 527.0 A | 462.9 A | 211.6 A | 162.9 A | 124.0 A | 0.0 |
| 5× shampoo | 417.4 A | 447.7 A | 768.0 B | 691.8 B | 554.0 B | 0.0 |
| 10× shampoo | n/a | n/a | 1245.2 C | 1177.7 C | 931.5 C | 0.0 |

2. Moisture (DVS) reduction. The table below demonstrates % moisture (DVS) reduction for the present invention composition vs control compositions. Hair treated with the shampoos containing the moisture active shows decreased moisture pickup at 90% humidity vs. control formulations.

|  | % water reduction vs control formula without SA | | |
|---|---|---|---|
|  | Formula L | Formula M | Formula O |
| 1X SH | 1.04% | 1.04% | 0.00% |
| 5X SH | 2.42% | 1.68% | 0.00% |
| 10X SH | 2.08% | 2.50% | 0.00% |

Cleansing of hair with shampoo containing a Moisture Control Material, such as salicylic acid, result in absorption of smaller quantity of moisture than hair that is cleaned with shampoo having the similar composition but which does not contain the Moisture Control Material, as it can be seen in the DVS data that are summarized in the above table. The tables above also indicate that shampoo compositions having lower pH (pH 4 instead of 6), allow for higher accumulation of the Moisture Control Material inside the hair over multiple shampoo cleansing cycles.

Leave-on Treatment Composition Preparation:

The leave-on treatment compositions are prepared by adding the Moisture Control Materials and perfume, if needed, into a 50:50 ethanol/water carrier and stirred until complete dissolution. The solution pH is adjusted using sodium hydroxide (50% w/w) to a final pH of 4.0-4.2. The Sepigel 305 is then added, if needed, and the solution is mixed using a high-speed-mixer for 2-5 minutes at 1800-2300 rpm until a uniform composition is obtained.

Leave-on Hair Treatment Protocol:

An amount of 0.20 g of each composition of Examples I to IV is spread via a syringe onto separate natural virgin brown hair switches weighing 2.0 g (dosage 0.10 g of solution per g of hair). The hair is allowed to air dry and then analyzed using the DVS method described above. The experiment is repeated for a dosage of 0.50 g of solution per g of hair. The hair in this case is also assessed by expert graders, as described below, in addition to the DVS analysis.

Hair Switch Feel Assessment Method:

The treated hair switches are kept at high humidity (above 85% RH) for 2 hrs and then ten expert graders are asked to rate each of them in terms of tactile feel based on a 5 point scale, 5 being the highest (best feel) and 1 being the lowest rating.

Leave-on Treatment Formulation:

| Raw Material | Leave-on treatment Control (wt./wt.) % | I (wt./wt.) % | II (wt./wt.) % | III (wt./wt.) % | IV (wt./wt.) % | V (wt./wt.) % | VI (wt./wt.) % | VII (wt./wt.) % |
|---|---|---|---|---|---|---|---|---|
| Distilled Water | QS | QS | QS | QS | QS | QS | QS | QS |
| Ethanol | 50.00 | 50.00 | 50.00 | 50.00 | 50.00 | 50.00 | 50.00 | 50.00 |
| Polyacrylamide & C13-14 Isoparaffin & Laureth-7 (Sepigel 305) | 1.85 | 1.85 | 1.85 | 1.85 | 1.85 | 1.85 | 1.85 | 1.85 |
| Perfume | 0.46 | 0.46 | 0.46 | 0.46 | 0.46 | 0.46 | 0.46 | 0.46 |
| Salicylic acid | 0 | 2.0 | 0 | 0 | 2.0 | 2.0 | 0.0 | 0.0 |
| 5-Chlorosalicylic acid | 0 | 0 | 2.0 | 0 | 0 | 0 | 2.0 | 2.0 |
| 2,4-Dihydroxy-benzoic acid | 0 | 0 | 0 | 2.0 | 0.15 | 0.15 | 0.15 | 0.15 |
| Oleic acid | 0 | 0 | 0 | 0 | 0 | 0.25 | 0 | 0.25 |
| 2-Hexyl-1-decanol | 0 | 0 | 0 | 0 | 0 | 0.25 | 0 | 0.25 |
| Final pH | 4.2 | 4.2 | 4.2 | 4.2 | 4.2 | 4.2 | 4.2 | 4.2 |
| % Water Reduction versus Leave-on Treatment Control at dose of 0.10 g of composition for 1.0 g of hair | — | — | — | — | 4 | 5 | 5 | 7 |
| % Water Reduction versus Leave-on Treatment Control at dose of 0.50 g of composition for 1.0 g of hair. Control is dosed at 0.50 g of composition for 1.0 g of hair | — | 4 | 5 | 5 | 9 | 8 | 10 | 10 |

-continued

| | | | | | | | | |
|---|---|---|---|---|---|---|---|---|
| Feel Rating Leave-on Treatment Control at dose of 0.10 g of composition for 1.0 g of hair | 1 | 1 | 2 | 2 | 2 | 3 | 2 | 4 |

| Formula Example | VIII | IX | X | XI | XII | XIII |
|---|---|---|---|---|---|---|
| Raw Material | | | | | | |
| Distilled Water | QS | QS | QS | QS | QS | QS |
| Ethanol | 50.0 | 50.0 | 50.0 | 50.0 | 50.0 | 50.0 |
| 5-Chlorosalicylic acid | 1.0 | | | 1.0 | 1.0 | 1.0 |
| 2-Hexyl-1-decanol | | | 5.0 | 5.0 | | 5.0 |
| Isostearyl Isostearate | | 2.0 | | | 2.0 | 2.0 |
| Final pH | 4 | 4 | 4 | 4 | 4 | 4 |
| % Water Reduction versus Leave-on Treatment Control at dose of 0.10 g of composition for 1.0 g of hair | 1.3 | 0.7 | 1.0 | 2.0 | 1.4 | 3.0 |
| Feel Rating (on 5 scale point with 5 as highest and 1 as lowest) | 1 | 2 | 2 | 3 | 3 | 4 |

Results:

Formula I to XIII showed % water reduction at high humidity. Higher % water reductions are observed in hair treated with higher doses of leave-on Formulas I-XIII The feel assessment results indicate that combinations of (a) 5-Chlorosalicylic acid and 2-hexyl-1-decanol;

(b) 5-Chlorosalicylic acid and isostearyl isostearate;

(c) 5-Chlorosalicylic acid and 2-hexyl-1-decanol and isostearyl isostearate provide, not only water absorption reduction (resulting in frizz benefit), but also tactile feel benefit. This is shown by the feel comparisons of (a) Example XI versus Examples VIII and IX, (b) Example XII versus Examples VIII and X, and (c) Example XIII versus Examples VIII, IX and X.

Additional Evaluations

Additional leave-on treatment compositions are prepared (Tables 1 and 2) according to the procedure described above, which are used to treat hair switches using the procedure described above (amount of 0.10 g of composition per g of hair). The switch is kept at high humidity (above 85%) for 2 hours. Then, ten experts are asked to rate each hair switch in terms of frizz, clean feel, and greasy feel, based on a 5 point scale, 5 being the highest and 1 being the lowest rating. Acceptable values are:

For frizz, less than 2 (lower number corresponds to less frizz);

For no greasy feel less than 3, (lower number corresponds to less greasy feel), and For clean feel greater than 3 (higher number corresponds to cleaner feel).

TABLE 1

| | Class I Compounds | | | | | |
|---|---|---|---|---|---|---|
| | Formula Example | | | | | |
| Raw Material | Control | XIV | XV | XVI | XVII | XVIII |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| 5-Chlorosalicylic acid | 0% | 1% | 0% | 0% | 0% | 0% |
| Salicylic acid | 0% | 0% | 1% | 0% | 0% | 0% |
| 4-Hydroxybenzenesulphonic acid | 0% | 0% | 0% | 1% | 0% | 0% |
| 2,4-Dihydroxybenzoic acid | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 1 | 2 | 2 | 2 | 4 |
| Frizz | 4 | 2 | 1 | 2 | 2 | 3 |
| Clean Feel | 4 | 4 | 3 | 4 | 4 | 1 |

Results of Hair Switch Rating from Class I Molecules:

Molecules (5-chlorosalicylic acid, salicylic acid, 4-hydroxybenzenesulphonic acid, 2,4-dihydroxybenzoic acid) from Class I provide hair benefits. More specifically, Table 1 shows that hair treatments with 5-chlorosalicyclic acid, salicylic acid, 4-hydroxybenzenesulfonic acid and 2,4-dihydroxybenzoic acid provide fizz protection with clean feel and without greasy feel negative, as opposed to treatment with terminal aminosilicone, which provide some frizz benefit but with greasy feel negative and significantly less clean feel.

TABLE 2

| | Class II Compounds Formula Example | | | | | |
|---|---|---|---|---|---|---|
| Raw Material | Control | XIX | XX | XXI | XXII | XXIII |
| Distilled Water | 50.0% | 49.5% | 49.5% | 49.5% | 49.5% | 49.5% |
| Ethanol | 50.0% | 49.5% | 49.5% | 49.5% | 49.5% | 49.5% |
| Isostearyl isostearate | 0% | 1% | 0% | 0% | 0% | 0% |
| 2-Hydroxyethyl salicylate | 0% | 0% | 1% | 0% | 0% | 0% |
| Octyl salicylate | 0% | 0% | 0% | 1% | 0% | 0% |
| 2-Hexyl-1-decanol | 0% | 0% | 0% | 0% | 1% | 0% |
| Terminal Amino Silicone | 0% | 0% | 0% | 0% | 0% | 1% |
| Composition pH adjusted to | 4.2 | 4.2 | 4.2 | 4.2 | 4.2 | 4.2 |
| Greasy Feel | 2 | 2 | 2 | 2 | 3 | 4 |
| Frizz | 4 | 2 | 2 | 1 | 1 | 3 |
| Clean Feel | 4 | 3 | 3 | 3 | 3 | 1 |

Results of Hair Switch Rating from Class II Molecules:

Molecules (Isostearyl isostearate, 2-hydroxylethyl salicylate, octyl salicylate, 2-hexyl-1-decanol) from Class II provide hair benefits. More specifically, Table 2 shows that hair treatment with isostearyl isostearate, 2-hydroxyethyl salicylate, octyl salicylate, and 3-hexyl-1-decanol provide frizz protection with clean feel and without greasy feel negative, as opposed to treatment with terminal aminosilicone, which provide some frizz benefit but with greasy feel negative and significantly less clean feel.

Evaluation of Hair Friction

Leave-on formulation containing Moisture Control Material and Silicone oil shows improvement in dry feel compared to untreated hair. This is concluded by measurement of dry hair friction. For this evaluation, natural virgin brown hair switches (4.0 g) are washed with clarifying shampoo, and then treated with leave-on treatment of composition XXIV according to the protocol described above. Before the evaluation, the switches are air dried overnight in a controlled temperature and humidity room (22° C./50% RH). The friction force (grams) between the hair surface and a urethane pad along the hair is measured, with three measurements per switch using an Instron Tester instrument (Instron 5542, Instron, Inc, Canton, Mass., USA).

TABLE 3

| | Hair Friction | |
|---|---|---|
| | Formula Example | |
| Raw Material | XXIV | Control Hair-No Treatment |
| Distilled Water | 49.5% | |
| Ethanol | 49.5% | |
| 2,4 dihydroxybenzoic acid | 1% | |
| Silicone oil | 0% | |
| Composition pH adjusted to | 4.2 | |
| Average Force (g) | 40 | 55 |

As Table 3 indicates, treatment of hair with leave-on composition containing Moisture Control material and silicone oil results in reduced hair friction, which indicates improved dry feel.

It is known that organic hydrophobic molecules that are naturally present inside the hair (e.g. as part of Cell Membrane Complex lipids) contribute to its strength and integrity. It is also known that cosmetic treatments, such as oxidative coloring and permanent shaping result in reduction of the concentration of such hydrophobic material from hair. Thus, penetration of hydrophobic materials (e.g. Class II materials) inside the hair can contribute to lipid replenishment, which, at the same time, reduces water uptake to deliver moisture or frizz control benefit. Combination of different Class II materials e.g. benzyl alcohol, 2-hexyl-1-decanol, isostearyl isostearate, have multi-functionality of penetration, getting embedded into lipid of hair and also increasing the penetration of other hydrophobic materials like oleic resulting in further increase hydrophobicity of the hair interior.

Leave on Composition Containing Gel Matrix Preparation:

One of Example of the leave on formulation compositions can be prepared by any conventional method well known in the art containing gel matrix. The cationic surfactants and the fatty alcohols are mixed together and heated to from about 66° C. to about 85° C. to form an oil phase. Separately, the disodium EDTA, the Methylchloroisothiazolinone (preservative) and the water are mixed and heated to from about 20° C. to about 48° C. to form an aqueous phase. The oil phase is mixed into the water phase under high shear to form the gel matrix. The remaining of the components are added into the gel matrix with agitation. Then, the composition is cooled down to room temperature.

TABLE 4

| | Moisture control materials in leave on formulation containing Gel Matrix | | |
|---|---|---|---|
| | | Formula Example | |
| Raw Material | Active % | XXV (wt./wt.) % | XXVI (wt./wt.) % |
| Hydroxyethyl cellulose[1] | 80 | 0.400 | 0.400 |
| Cetyl Alcohol[2] | 90 | 0.575 | 0.575 |
| Stearyl Alcohol[3] | 97 | 0.383 | 0.383 |
| Benzyl Alcohol[4] | 99 | 0.400 | 0.400 |

TABLE 4-continued

Moisture control materials in leave on formulation containing Gel Matrix

| | | Formula Example | |
|---|---|---|---|
| Raw Material | Active % | XXV (wt./wt.) % | XXVI (wt./wt.) % |
| Disodium EDTA, Dihydrate[5] | 99 | 0.127 | 0.127 |
| Glyceryl monostearate (PoloxWSR N-10)[6] | 1.5 | 0.299 | 0.299 |
| Terminal Amino Silicone[7] | 90-100 | 2 | 2 |
| Perfume | | 0.550 | 0.550 |
| Salicylic acid[8] | 99.5 | 0 | 2.0 |
| Isostearyl Isostearate[11] | 100 | 0 | 1.0 |
| 2-hexyldecanol[12] | 97 | 0 | 5.0 |
| Purified Water | | Q.S. | Q.S. |
| % Water Reduction versus XIV (control) at dose of 0.1 g of composition for 1 g of hair | | — | 4 |
| pH | | 5.2 | 5.2 |
| % Frizz Reduction | | | 20 |

[1]Natrosol ™ hydroxyethylcellulose Supplied by Ashland (Kentucky, US)
[2]Supplied by P&G Chemicals
[3]Supplied by P&G Chemicals
[4]Supplied by Ineos Maastricht BV (Maastricht NL)
[5]Trilon BD Powder supplied by BASF SE (Ludwigshafen, DE)
[6]POLYOX ™ WSR N-10 (Glyceryl monostearate) supplied by Dow chemicals (Michigan US)
[7]Y-14945 supplied by Momentive Performance Materials
[8]Supplied by API Corporation
[9]Supplied by Sigma Aldrich
[10]Supplied by Sigma Aldrich
[11]Crodamol ISIS supplied by Croda
[12]Isofol 16 supplied by Sasol (Brunsbuettel, DE)

Results:

Hair Switches that are treated with leave on treatment of example XXVI, using the leave on hair treatment protocol described in page 17-18, shows % water reduction by DVS method of 4% vs hair treated with example XXV control.

Penetration of Moisture Control Material

In an embodiment of the present invention, compositions can comprise of glycols, polyglycols, urea, ethers or mixture thereof. These materials increase penetration of moisture control actives such as salicylic acid, 5-chloro salicylic acid, improving their performance. Propylene glycol, butylene glycol and other glycols, increase penetration of 5-chlorosalicylic acid inside hair as it acts as carrier for the actives to penetrate further. As active penetration increases, there is an increase in efficacy of the active, i.e. there is increase in % water reduction as shown below in Table 5. Table 5 shows the amount of 5-chlorosalicylic acid that penetrates inside oxidatively damaged hair after hair treatment with two different compositions. It also shows the % water reduction observed after the treatment versus treatment with control leave-on treatment compositions. These results demonstrate that 5-chlorosalicylic acid penetrates 4 times more in the presence of propylene glycol and there is an increase in % water reduction as measured by DVS of approximate 4 times more than without propylene glycol. Another example of material that enhances the penetration of moisture control material is 2-hydroxyethyl urea. Leave on treatment composition that contain 2% of 2-hydroxyethyl urea increases the penetration of salicylic acid inside hair by 14% compared to the corresponding composition that does not contain 2-hydroxyethyl urea (see example XXIX and XXX).

TABLE 5

Enhancing of hair penetration of Moisture Control Material in oxidatively damaged (bleached) Caucasian hair

| | Formula Example | | | | |
|---|---|---|---|---|---|
| Raw Material | Control | XXVII | XXVIII | XXIX | XXX |
| Distilled Water | 50.0% | 48.93% | 43.9% | 48.93% | 48.00% |
| Ethanol | 50.0% | 48.93% | 43.9% | 48.93% | 48.00% |
| 5-Chlorosalicylic acid | 0.0% | 2.0% | 2.0% | 0.0% | 0.0% |
| 2-hydroxyethyl urea | 0.0% | 0.0% | 0.0% | 0.0% | 2.0% |
| Salicylic acid | 0.0% | 0.0% | 0.0% | 2.0% | 2.0% |
| 2,4-Dihydroxybenzoic acid | 0.0% | 0.15% | 0.15% | 0.0% | 0.0% |
| Propylene glycol | 0.0% | 0% | 10% | 0% | 0.0% |
| Composition pH adjusted to | 4.2 | 4.2 | 4.2 | 4.2 | 4.2 |
| % Water Reduction versus control treatment | — | 0.67% | 3% | — | — |
| Amount of 5-chlorosalicylic acid inside the hair (mg/g of hair) | — | 1 | 3.97 | — | — |
| Amount of Salicylic acid inside hair (mg/g of hair) after 5 cycles | — | — | — | 4.7 | 5.6 |

The penetration amount of 5-chlorosalicylic acid is determined using penetration method disclosed in the Evaluation Methods for active penetration inside hair.

In addition to the increase of the penetration amount of the moisture control material, the presence of glycol in the composition prevents the crystallization of part of the moisture control material in the surface of the hair. Such crystallization causes a non-smooth, negative hair feel, which may be perceived by consumers as hair damage or lack of conditioning.

It has been observed that in an embodiment of the present invention the presence of propylene glycol may provide penetration enhancement for Molecular Class I and Class II materials.

It is further noted that terms like "alternatively," "usually", "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

What is claimed is:

1. A shampoo composition for hair frizz reduction comprising: from about 0.1% to about 20% of a moisture control material or mixture of moisture control materials wherein the moisture control material is selected from one or more of the following:

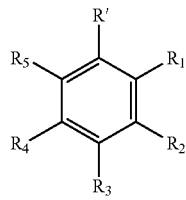

wherein R' is —COOY, sulfonic acid, or C═CH—COOY, Y is hydrogen or a metal ion, $R_1$, $R_2$, $R_3$, $R_4$, $R_5$ is hydrogen, methyl, ethyl, propyl, vinyl, allyl, methoxy, ethoxy, hydroxyl, halogen, sulfate, sulfonate, nitro, or —CH═CH—COOR, and wherein the moisture control material is an polar, acidic material and further wherein the moisture control material has a % Protein binding higher than 20 and Molecular Volume lower than 500 and Partition coefficient octanol to water (log P) lower than 3 and hydrogen binding higher than 10 and pKa lower than 5.0 wherein the moisture control material comprises salicylic acid in combination with 2,4-dihydroxybenzoic acid wherein shampoo composition further comprises a material selected from the group consisting of glycols, polyglycol and 2-hydroxyethyl urea or mixture thereof.

2. A shampoo composition according to claim 1 wherein the concentration of the Moisture Control Material or the concentration of the mixture of Moisture Control Material is from about 0.5% to about 8%.

3. A shampoo composition according to claim 1 wherein the concentration of the Moisture Control Material or the concentration of the mixture of Moisture Control Material is from about 0.5% to about 5%.

4. A shampoo composition according to claim 1 wherein the polar, acidic material further comprises material selected from the group consisting of 3-hydroxybenzoic acid, gallic acid, 3-aminobenzoic acid, 4-aminobenzoic acid, 2,5-dihydroxybenzoic acid, 3,4-dihydroxybenzoic acid, 3,5-dihydroxybenzoic acid, 2,6-dihydroxybenzoic acid, 5-chlorosalicylic acid, trans-ferulic acid, p-coumaric acid, 4-hydroxybenezesulphonic acid, 3-chloro-4-hydroxybenzoic acid, 3,5-dihydroxybenzoic acid, 2,5-dihydroxyterepthalic acid, and mixtures thereof.

5. A shampoo composition according to claim 4 wherein the moisture control material is 5-chlorosalicylic acid.

6. A shampoo composition according to claim 1 further comprising 5-chlorosalicylic acid and silicone.

7. A shampoo composition according to claim 1 wherein the composition has a pH from about 3 to about 5.5.

8. A shampoo composition according to claim 1 wherein the composition has a pH from about 3.5 to about 5.0.

9. A shampoo composition according to claim 1 wherein the composition further comprises a silicone.

10. A shampoo composition according to claim 1 wherein the composition further comprises materials selected from the group consisting of conditioning materials, organic conditioning materials, solvents, rheology modifier, suspending agent, thickeners, hair health actives, anti-dandruff actives, anti-oxidants, pigments, abrasives, absorbents, biological actives, buffering agents, chelating agents, opacifying agents, pH adjusters, vitamins, chelants, perfumes, brighteners, enzymes, sensates, attractants, anti-bacterial agents, dyes, bleaches and mixtures thereof.

11. A shampoo composition according to claim 1 wherein the composition further comprises a cationic surfactant system.

12. A shampoo composition according to claim 1 wherein the shampoo composition further comprises a gel matrix comprising:
  i. from about 0.1% to about 20% of one or more fatty alcohols, by weight of said hair care composition;
  ii. from about 0.1% to about 10% a cationic surfactant system of, by weight of said hair care composition; and
  at least about 20% of an aqueous carrier, by weight of said hair care composition.

13. A shampoo composition according to claim 1 comprising salicylic acid from about 0.5% to about 2% in combination with 2-hydroxyethyl urea from about 0.2% to about 10%.

14. A shampoo composition according to claim 1 wherein hair treated with the composition results in a decrease moisture pickup at 90% humidity as compared to a control with no moisture control materials.

15. A shampoo composition according to claim 1 wherein at a pH of 4 there is an increase of moisture control material penetration into hair over multiple shampoo cleansing cycles.

16. A method of treating hair using the shampoo composition of claim 1 wherein hair treated with the shampoo composition results in a decrease moisture pickup determined by a Dynamic Vapor Sorption (DVS) method as compared to a control with no moisture control materials.

* * * * *